(12) United States Patent
Murray et al.

(10) Patent No.: US 7,202,226 B2
(45) Date of Patent: Apr. 10, 2007

(54) AUGMENTATION OF WOUND HEALING BY ELF-4E MRNA AND EGF MRNA

(75) Inventors: Mary Theresa Murray, Grosse Pointe, MI (US); Scott Alexander Dulchavsky, Grosse Pointe Park, MI (US)

(73) Assignee: Detroit R & D, Detroit, MI (US)

( * ) Notice: Subject to any disclaimer, the term of this patent is extended or adjusted under 35 U.S.C. 154(b) by 568 days.

(21) Appl. No.: 10/001,563

(22) Filed: Oct. 23, 2001

(65) Prior Publication Data

US 2002/0071834 A1 Jun. 13, 2002

Related U.S. Application Data

(60) Provisional application No. 60/242,662, filed on Oct. 23, 2000.

(51) Int. Cl.
*A61K 48/00* (2006.01)
(52) U.S. Cl. ...................................................... 514/44
(58) Field of Classification Search ................. 514/44; 536/321
See application file for complete search history.

(56) References Cited

OTHER PUBLICATIONS

Steenos, H. (Scand. Journal Plastic Reconst. Hand Surgery, 1994; vol. 28, pp. 95-105).*
Andree C, Swain WF, Page CP, Macklin MD, Slama J, Hatzis D, Eriksson E. (1994) Proc Natl Acad Sci USA 91:12188-12192.
Bell GI, Gong NM, Stermien MM. (1986) Nucleic Acid Res 14(21):8427-8433.
Bennett NT, Schultz GS. (1993). Am J Surg 165;728-734.
Brown GL, Curtsinger LJ, White M, Mitchell RO, Pietsch J. (1988) Ann Surg 208(6);788-793.
Callis J, Fromm M, Walbot V. (1987) Nucleic Acids Res 15(14):5823-5831.
Cheng L, Ziegelhoffer PR, Yang N-S. (1993) Proc Natl Acad Sci USA 90:4455-4459.
De Benedetti A., Rhodes R.E. (1990) Proc. Natl. Acad. Sci USA 87:8212-8216.
Hiremath, L. S.,. Rychlik W, Joshi, S, Domier, LL, Rhoads RE. (1989) J Biol Chem 264:1132-1138 (published erratum 264:21431).
Koromilas, A.E., Lazartis-Karatzas, A., Sonenberg, N. (1992) EMBO J. 11:4153-4158 (published erratum 11:5138).
Lazaris-Karatzas, A. Montine, K.S, Sonenberg, N. (1990) Nature 345:544-547.
Qui P, Ziegelhoffer P, Sun J, Yang NS. (1996). Gene Therapy 3:262-268.
Sohn R.L., Murray M.T., Schwarz, K., Nyitray J., Purray P., Franko A.P., Palmer K., Diebel L.N., Dulcavsky S.A. (2001) Wound Rep. Reg. 9:287-296.
Yang N-S, Burkholder J, Roberts B, Martinell B, McCabe D. (1990) Proc. Natl. Acad. Sci USA 87:9568-9572.

* cited by examiner

*Primary Examiner*—Jon E. Angell
(74) *Attorney, Agent, or Firm*—Kenneth I. Kohn; Kohn & Associates, PLLC

(57) ABSTRACT

There is provided a method of augmenting transient protein synthesis in a cell by delivering to the cell mRNA functionally related to protein production. Also provided is a method of augmenting transient protein synthesis in cells by increasing protein synthesis of growth factors from endogenous cellular mRNA and exogenous mRNA delivered to the cells. A treatment for transiently increasing protein production in cells, said treatment comprising mRNA functionally related to protein production is also provided. There is provided a method of augmenting wound healing by delivering mRNA functionally related to wound healing. Further provided is a therapeutic for transiently increasing protein synthesis in cells, said therapeutic comprising mRNA related to protein production.

2 Claims, No Drawings

AUGMENTATION OF WOUND HEALING BY ELF-4E MRNA AND EGF MRNA

CROSSREFERENCE TO RELATED APPLICATIONS

This application claims benefit under 35 USC §119 (e) of U.S. Provisional Patent Application Ser. No. 60/242,662, filed Oct. 23, 2000.

BACKGROUND OF THE INVENTION

1. Field of the Invention

The present invention relates to methods of augmenting protein synthesis. More specifically, the present invention relates to healing wounds by augmenting protein synthesis.

2. Description of Related Art

Wound healing is a complex process involving inflammation, recruitment of fibroblasts and macrophages, synthesis of collagen, and remodeling of the newly formed wound substrate.[4] Wound healing is believed to proceed at near maximal levels in the uncompromised host; however, numerous disease states and therapeutic interventions are associated with significant alterations in wound healing. Steroid, chemotherapeutic agents, diabetes, and ischemia all result in a reduction in collagen synthesis and decreased wound strength. Recent investigations have suggested that optimization of growth factor delivery in these problematic wounds may improve clinical outcome.

Naturally produced substances have been discovered which promote repair, healing and augmentation of tissues and organs. Such substances have been termed "growth factors". Growth factors, usually proteins, initiate programs of differentiation and/or development within an organism.

When referring to tissue repair, the appellation "growth factor" is a misnomer. Confusion in separating the biological processes of growth from the processes involved in repair, healing and augmentation is often caused by the use of the term "growth factors" to describe these proteins. Repair, healing and augmentation, as discussed in detail below, are distinct biological activities and are clearly distinguishable from growth. Growth in the biological sense is defined as progressive development from a lower or simpler to a higher or more complex form of organization. Tissues and organs "grow" from a few similar appearing cells to a complex organized structure, such as a kidney or an eye. For clarity, organs are defined as functional units of the body containing multiple cell types. Examples of organs include, for instance, kidneys, eyes, the liver, the heart, bone, skin and cartilage. Tissues are defined as functional units of the body that are made up of almost an entirely single cell type. For instance, connective and support tissues are derived from and comprised of almost entirely a single cell type, e.g. fibroblast or muscle cell.

Growth factors can stimulate wound healing. The process of wound healing begins immediately following surface lesion or after skin proteins become exposed to radiation, chemical damage or extreme temperatures. Wound healing requires close control of degradative and regenerative processes, involving numerous cell types and complex interactions between multiple biochemical cascades. Growth factors released in the traumatized area stimulate and promote the following: 1) cell migration into the wound area (chemotaxis); 2) proliferation of epithelial cells, muscle cells, endothelial cells, blood cells and fibroblasts (mito-genesis); 3) formation of new blood vessels (angiogenesis); and 4) matrix formation and remodeling of the affected region including re-epithelization by keratinocytes. Studies on animals have shown that exogenously added growth factors can accelerate the normal healing process, and studies on humans have shown that growth factors can heal previously incurable wounds. Factors capable of enhancing wound healing are particularly important in treatment of patients with chronic wounds which may require daily treatment, represent a constant source of pain to the patient, may lead to life threatening infection and are a significant medical expense. Chronic wounds are those which are slow-healing or which do not heal at all and are common to diabetics, cancer patients and those confined to bed for long periods of time. Treatment of chronic wounds may consume up to $4 billion per year in medical expenses in the United States alone.

Despite their beneficial effect on bone, cartilage, skin and connective and support tissue, the use of growth factors poses several problems. Growth factors, when systemically administered, affect non-target organs and may therefore elicit a variety of adverse side effects. For instance, one recent article expressed the opinion that TGF-β may contribute to the renal lesions found in glomerulone-phritis, the leading cause of kidney failure in people with diseases such as lupus, diabetes and hypertension. Skerrett (1991). Further problems with growth factors are their instability and tendency to break down once purified and stored for therapeutic use. Moreover, many of the amino acid sequences of growth factors vary between species and are consequently recognized as foreign by dissimilar, or heterologous, species. There is the constant danger of eliciting an immune response upon administration of heterologous growth factors. Furthermore, there is no evidence that parenterally administered growth factors target bone, cartilage, skin, and connective and support tissues. Parenteral administration refers to intravenous, intramuscular, intraperitoneal and subcutaneous administration.

As proteins, growth factors are not suitable for oral administration, since they are digested and destroyed before entering the blood stream. Growth factors cannot be satisfactorily administered as topical ointments except for skin wounds, because they are only slowly absorbed by the body and subsequently break down rapidly. Because of these and other problems, growth factors are typically administered intravenously. Since naturally occurring growth factors can after the function of many organs and tissues of the body, intravenous administration of growth factors affects many non-target organs. A therapeutically effective compound that directly targets bone, cartilage, skin and connective and support tissues when parenterally administered or that can be directly applied to the tissues or organs that need to be repaired, healed or augmented is highly preferred to currently available naturally occurring growth factors.

Wound healing is in large part mediated by growth factors that control cellular migration into the wound area or synthesis of wound structural or regulatory proteins.[3] EGF is a 53 amino acid polypeptide that acts as a chemotactic factor for keratinocytes, vascular smooth muscle cells and granulation derived fibroblast.[2] Application of EGF results in accelerated wound healing as determined by an increase in tensile strength of the wound in normal animals.[6]

Gene therapy using particle bombardment of nucleic acid-laden microcarriers with a gene gun allows intracellular delivery of DNA or RNA.[13] Such biolistic delivery is well suited for applications in wound healing where the application site is accessible.[6] DNA gene therapy has significant risks including insertional mutagenesis and uncontrolled promoter activity and promoter reactivation. Additionally, the problems detailed above have prevented others from attempting more detailed studies into the use of mRNA in this form of gene therapy.

Biolistic delivery and expression of a human EGF gene construct resulted in accelerated wound healing.[1] In this study an external sealed fluid filled wound chamber was used to protect the wound. Wounds treated with the human EGF plasmid pWRG1630 exhibited a 190-fold increase of EGF in the wound fluid and healed 20% faster than controls. EGF levels remained elevated for more than 8 days. It is noteworthy that the human EGF in vitro transcription vector created for these studies was derived from plasmid pWRG1630 therefore the EGF protein produced should have similar biological activity.

For wound healing applications, RNA mediated gene transfer is desirable as it avoids promoter expression uncertainty, and provides for a potent biologic effect for a finite therapeutic period without concerns of long-term deleterious effects. With the RNA delivery approach, target cells serve as a bioreactor for protein synthesis eliminating protein processing and modification difficulties noted with exogenously produced, recombinant products.[5] The mRNA delivery technique allows the use of more potent cellular factors or stimulants than previous possible as it is not associated with long term mutagenic concerns.[11]

Translation of mRNA is now recognized as a key regulatory step in gene expression. Initiation of translation is the rate-limiting step and therefore a major regulatory target. The eukaryotic initiation factor family eIF, binds to the ribosome subunit facilitating protein translation. The rate of protein synthesis of eukaryotic cellular mRNA is controlled by the initiation step of translation because the translation initiation factor eIF4E is rate limiting.[8] The activity of eIF4E is regulated by phosphorylation that is acted on by various growth factors.

Over-expression of eIF4E is associated with aberrant growth and morphology in HeLa cells and malignant transformation of NIH T3T cells.[7, 10] Moreover, increased levels of eIF4E have been noted in carcinoma specimens. This raises the possibility that chronic over-expression of eIF4E may be oncogenic therefore potential therapeutic applications of eIF4E gene therapy have not been suggested.

Not all mRNA transcripts are translated with equal efficiency due to structural constraints in the 5' untranslated region. These "weak" transcripts are hypothesized to be more dependent on eIF4E for translation, and their translational yield more responsive to increases in active eIF4E. Highly structured mRNAs that may be subject to this regulation include ones that encode growth factors (PDGF-b, ILGF-II, FGF-2, TGF-β, and VEGF), transcription factors (Ick, c-mos) and cell cycle regulators (CDK, p53).[9] A few growth-promoting proteins have been demonstrated to be regulated by the level of active eIF4E (cyclin D1, ornithine decarboxylase and P23). For this invention, it is important to note that EGF is not predicted to have significant secondary structure in its 5' untranslated region, and regulation of EGF by eIF4E has never been suggested, especially in light of the potential oncogenic effects.

Referring specifically to TGF-β, this growth factor belongs to a family of growth factors that produce multiple biological effects, including mitogenesis, growth regulation, regulation of cartilage and bone formation, chemotaxis and induction or inhibition of cell differentiation, depending on the tissue or cell type and the presence or absence of other growth factors. Most of the published work on TGF-β relates to its wound healing capabilities. However, TGF-β plays other physiological roles, as shown by the fact that it is known to be contained and produced within bone. Seyedin et al., "Cartilage-Inducing Factor", J. Biol. Chem., 261: 5693–5695 (1986); and Robey et al., "Factor-Type .beta. (TGF-β) in vitro", J. Cell Biol., 105: 457–463 (1987). TGF-β will enhance bone formation. Sporn et al., "Some Recent Advances in the Chemistry and Biology of Transforming Growth Factor-.beta.", J. Cell Biol., 105: 1039–1045 (1987). Other members of the TGF-β family of growth factors, notably BMP, have also been shown to enhance bone formation. Wozney et al., "Novel Regulators of Bone Formation: Molecular Clones and Activities", Science, 242: 1528–1533 (1988).

With specific regard to bone resorption, recent studies with purified cell membranes have shown that gallium nitrate $(Ga(NO_3)_3)$ can block the transport of hydrogen atoms across osteoclast cell membranes. This hydrogen atom transport would otherwise lead to the dissolution of the mineral matrix of bone, thereby releasing calcium ions into the blood. Although TGF-β affects bone repair, healing and augmentation, it has not been shown to block transport of hydrogen atoms across osteoclast cell membranes. In fact, TGF-β has not been demonstrated to be a clinically effective antiresorptive agent capable of preventing accelerated bone breakdown and disordered calcium homeostasis. Indeed, unlike previously shown activity of gallium nitrate, TGF-β inhibits the differentiation and proliferation of osteoclastic cells, leading to decreased osteoclast cell numbers. Chenu et al., "Transforming Growth Factor Beta Inhibits Formation of Osteoclast-Like Cells in Long-Term Human Marrow Cultures", Proc. Natl. Acad. Sci. USA, 85: 5683–5687 (1988). By contrast, rats treated with gallium nitrate have normal or increased numbers of osteoclasts. Cournot-Witmer et al., "Bone Modeling in Gallium Nitrate Treated Rats", Calcif. Tis. Int., 40: 270–275 (1987).

There is no direct relationship between the deposition of the mineral component of bone and biologic bone repair, healing and augmentation. The mineral component of bone is made up of hydroxyapatite, a crystalline, inorganic complex of calcium and phosphate. Hydroxyapatite crystals "grow" in size in the physical process of accretion (i.e., addition) of new atoms of calcium and phosphate. Calcium accretion onto crystalline hydroxyapatite of bone is a passive physical-chemical process that does not require living cells. The synthesis of new matrix components, which requires living cells, the activation of specific genes and the de novo synthesis of proteins from organic elements, is unrelated to calcium accretion. The basic building blocks for matrix synthesis come from living cells and have, for the most part, been synthesized de novo by those cells. Disorders of calcium homeostasis, therefore, affect only the inorganic matrix of bone and are unrelated to repair, healing and augmentation in the biologic sense. Mechanisms involved in repair, healing and augmentation of the organic matrix of bone, cartilage, skin and connective and support tissues represent biologic processes that are different and distinct from mechanisms involved in calcium accretion.

Several pharmaceutical agents, including cisplatin, mithramycin, calcitonin, and bisphosphonates, have been shown to inhibit resorption of bone mineral matrix. None of these agents, however, have a proven beneficial effect on bone formation or wound healing. Cisplatin and mithramycin are cytotoxic agents which, when injected parenterally, act by killing the cells responsible for tissue breakdown, as well as those responsible for tissue formation. Calcitonin, a naturally produced hormone, transiently inhibits the activity of bone-resorbing cells (osteoclasts) to prevent bone breakdown. Calcitonin increases excretion of calcium by the kidneys and thus accelerates calcium loss from the body.

Bisphosphonates are a class of synthetic compounds that inhibit bone resorption. Etidronate (EHDP) is currently the only bisphosphonate approved for use in the United States. Osteoporosis patients who have been treated with EHDP, however, have shown a 50% increase in vertebral fracture rates in the third year. See, e.g., "Update: Bisphosphonates Editronate evaluated by FDA", Lunar News, March 1991. The possible ineffectiveness of EHDP over long-term treatment tends to indicate that agents that inhibit bone resorption do not strengthen bone in a clinically significant manner, and in fact, may tend to weaken bone. Further, EHDP inhibits matrix-forming cells. Schenk et al., "Effect of Ethane 1-hydroxy-1,1-diphosphate (EHDP) and Dichloromethylene Diphosphonate (Cl$_2$ MDP) on the Calcification and Resorption of Cartilage and Bone in the Tibial Epiphysis and Metaphysis of Rats", Calcif. Tis. Res., 11: 196–214 (1973).

Fluoride-containing salts have been extensively tested for their effects on matrix-forming cells. Treatment with fluoride, however, results in the production of a highly abnormal (woven-type) bone matrix structure. Such fluoride-induced bone is weaker than normal bone. Jowsey et al., "Some Results of the Effect of Fluoride on Bone Tissue in Osteoporosis", J. Clin. Endocrinol., 28: 869–874 (1968). Indeed, a recently completed study showed that fluoride did not significantly reduce skeletal fractures in osteoporotic women. Kleerekoper et al., "Continuous Sodium Fluoride Therapy Does Not Reduce Vertebral Fracture Rate in Post-menopausal Osteoporosis", J. Bone and Min. Res., 4:S376 (1989).

Estrogen replacement therapy has resulted in increased bone mass in estrogen-deficient, post-menopausal women. Lindsay et al., "Long-Term Prevention of Postmenopausal Osteoporosis by Estrogen Treatment", Lancet, 1: 1038–1041 (1976). Estrogen directly affects bone-forming cells to increase matrix elements, such as collagen, and to increase an endogenous growth factor, insulin-like growth factor-I (IGF-1). Ernst et al., "Estradiol Effects on Proliferation, Messenger RNA for Collagen and Insulin-like Growth Factor-I, and Parathyroid Hormone-Stimulated Adenylate Cyclase Activity on Osteoblastic Cells from Calvariae and Long Bones", Endocrinol., 125: 825–833 (1989). However, the benefits of estrogen treatment are limited to perimenopausal women, those women who are about to enter or who have entered menopause. Furthermore, estrogen treatment is associated with increased risk of uterine and breast cancer. Bergkvist et al., "The Risk of Breast Cancer After Estrogen and Estrogen-Progestin Replacement", N. E. J. Med., 321: 293–297 (1989).

In summary, exogenous growth factors, while capable of inducing synthesis of new matrix components in a manner that simulates natural, normal, conditions of repair, healing and augmentation of organs and tissues, have proven to be difficult to administer and tend to cause side effects. Further, various pharmaceutical agents have proven unsuccessful in inducing synthesis of new matrix components in a manner that simulates natural, normal, conditions of repair, healing and augmentation of organs and tissues.

It would therefore be useful to develop biolistic delivery mechanisms for delivery of mRNA to a wound, or other site in need of transient increased protein synthesis, for increased cellular translation of endogenous mRNA to augment wound healing.

SUMMARY OF THE INVENTION

According to the present invention, there is provided a method of augmenting transient protein synthesis in a cell by delivering to the cell mRNA functionally related to protein production. Also provided is a method of augmenting transient protein synthesis in cells by increasing protein synthesis of growth factors from endogenous cellular mRNA and exogenous mRNA delivered to the cells. A treatment for transiently increasing protein production in cells, comprising mRNA functionally related to protein production, is also provided. There is provided a method of augmenting wound healing by delivering to a wound mRNA related to wound healing. Further provided is a therapeutic for transiently increasing protein synthesis in cells, the therapeutic comprising mRNA related to protein production.

DETAILED DESCRIPTION OF THE INVENTION

The present invention generally provides a method for transiently augmenting protein production in a cell. More specifically, the present invention provides a method of augmenting wound healing by intracellular delivery of mRNA encoding the translation initiation factor eIF4E. This biolistic treatment of wounds with eIF4E mRNA augments wound healing in animals that are either normal or impaired in their wound healing ability.

By "augmenting" as used herein, the term is intended in include, but is not limited to, increasing or sustaining an increased production level of the augmented item. In other words, the present invention increases protein production or causes a wound to heal more readily. The effect of the treatment of the present invention is transient. In other words, there is no long-term increase in protein synthesis. This is created because of the present invention utilizes mRNA rather that DNA. Previously, when DNA has been used to augment protein synthesis, the DNA would integrate into the cell's genome and create long-term mutations. The mutations can potentially lead to cancerous growth. Therefore, it is imperative that the augmentation is transient, such as that created by the present invention.

Additionally, the mRNA utilized in conjunction with the present invention can increase protein synthesis in one of three ways. First, the mRNA can encode translation initiation factors, which can increase protein synthesis from endogenous cellular mRNA. This therefore functions by potentiating the protein synthesis of the endogenous mRNA. Second, the mRNA can encode exogenous growth factors, thereby increasing protein production in the cell utilizing the exogenous growth factor mRNA. And in a third embodiment, both types of mRNA can be used in conjunction with one another. This combination treatment has been shown to have a synergistic effect.

The mRNA can be delivered in any means known to those of skill in the art. This can include particle acceleration, direct application, or the inclusion of the treatment in a substance applied to cells for example, glue used post surgery, a band-aid, etc.

The present invention provides growth factors, which are necessary for wound healing. As defined in the background, growth factors are known to those of skill in the art to include, but are not limited to, PDGF-β, ILGF-II, FGF-2, TGF-β, and EGF. Alternatively, the growth factor can be a chemical, either natural or synthetic, which creates the same effect. In other words, a growth factor is any chemical that stimulates wound healing.

Also provided by the present invention is a translation initiation factor. A translation initiation factor is a product that initiates or begins protein synthesis. The translation initiation factor can be the factor specifically disclosed herein, namely, eIF4E, or it can be any chemical that is capable of initiating protein synthesis.

The mRNA of the present invention functionally relates to protein synthesis. More specifically, the mRNA encodes for proteins that are desired to be upregulated in a cell. In other words, the mRNA encodes proteins that are required to be expressed in a cell. For example, the mRNA can encode for proteins necessary for wound healing, to promote cell death, or any other desired effect that is based upon or relies upon protein synthesis.

Specifically, the present invention also provides a method to augment wound healing by intracellular delivery of mRNA encoding translation initiation factor eIF4E in combination with mRNA encoding cellular growth factors such as EGF. Biolistic treatment of incisional wounds with eIF4E mRNA and EGF mRNA augments wound healing in normal animals to a greater extent than animals treated with eIF4E mRNA or EGF alone. This synergistic effect was not predicted. If fact, based upon the prior art, it was unexpected that mRNA would have a predictable effect in vivo.

Epidermal growth factor (EGF) is recognized as a particularly useful treatment additive in wound treatment systems because of its role in promoting growth of epidermal skin tissue. Naturally occurring mature EGF is a 53 amino acid long polypeptide produced in vivo as the processed product of a very large (1200 amino acids long) precursor protein. Early wound-healing systems introduced purified mature EGF as a treatment additive directly into wounds. However, the cost of treatment with mature EGF was considered to be high since the polypeptide has a short half-life in wounds. In addition, it is difficult to purify, store and administer large quantities of natural mature EGF for use in a wound treatment system as a result of its lability.

Application of translation initiation factor eIF4E in wound healing was not an obvious extension of any previous work. Over-expression of eIF4E is known to stimulate proliferation and possibly oncogenic transformation. The application of eIF4E mRNA biolistic delivery to augment wound healing is utilized to increase the intracellular level of eIF4E and significantly increase translation of proteins essential for the wound healing response from the endogenous mRNA.

Application of EGF protein and EGF gene therapy has documented efficacy for improved healing.[1, 4] Biolistic delivery of EGF mRNA for improved wound healing was thought to have little possibility of success. This is due to the 1) highly unstable nature of mRNA that would likely be degraded as it passes through the ribonuclease laden blood of a wound, 2) the relatively low level of protein produced from biolistic mRNA delivery in past experiments, and 3) the high level of EGF protein produced in biolistic DNA delivery of EGF that was required for improved wound healing in previous work.[1, 11] Therefore augmentation of wound healing by EFG biolistic mRNA delivery was not an obvious extension of past work.

One method of intracellular delivery of mRNA is biolistic delivery using microcarriers coated with mRNA and this is used as an example. Human eIF4E mRNA is prepared by in vitro translation of the plasmid pTCEEC with a 5' cap and polyadenylated at its 3' end.[8] A human EGF chimera containing the secretory domain of human growth factor fused with a FLAG epitope tag and mature EGF was constructed in an in vitro transcription vector to encode a 3' poly(A) tail and used to generate 5' capped EGF mRNA.[12] The mRNA is coated on microcarriers and propelled into the incisional site using a Helios Gene Gun. Biolistic mRNA delivery is used as an example for intracellular mRNA delivery however other methods of mRNA delivery would also be suitable for this method of augmentation of wound healing by eIF4E mRNA. A single discharge of microcarriers delivered 1 microgram of each mRNA.

The Helios gene gun is a convenient, hand-held device that provides rapid and direct gene transfer into a range of targets in vivo. The unit uses an adjustable low-pressure helium pulse to sweep DNA- or RNA-coated gold microcarriers from the inner wall of a small plastic cartridge directly into the target. Sample preparation is also efficient. The preparation use a tubing prep station and a tubing cutter included in the system to make up to 50 sample cartridges at one time, with known amounts of DNA or RNA and gold microcarriers inside each cartridge. Then, up to 12 DNA or RNA-coated gold cartridges are loaded into the holder, the holder is inserted into the device, and the device is fired. The power and versatility of this instrument match its speed, since you can coprecipitate different nucleic acids onto the gold and thus deliver nucleic acids carrying various traits all in one experiment. Targeted gene delivery is now a reality for in vivo research applications.

In the delivery, the helium pulse sweeps the DNA- or RNA-coated gold microcarriers from the inside wall of the sample cartridge. The microcarriers accelerate for maximum penetration as they move through the barrel, while the helium pulse diffuses outward. The spacer maintains the optimal target distance for in vivo applications and vents the helium gas away from the target to minimize cell surface impact. Modifying the genetic makeup of cells through gene transfer with the Helios gene gun allows in vivo targets to directly take on new or enhanced functions. This capability is particularly useful for research efforts to broaden understanding in gene therapy, especially for cancer biology, wound healing, and disease. The Helios gene gun also enhances DNA vaccination (genetic immunization), as it operates via skin bombardment, requires only microgram amounts of DNA, and eliminates the need for tedious protein purification. Both humoral (antibody-based defenses in blood and lymph systems) and cell-mediated immunities (CTL responses) have been demonstrated in animals using this technology; see Particle Delivery References. Several instrument designs have been used in recent years; thus cell penetration, gene expression, and other measures of performance vary with the particle acceleration device model used.

The Helios gene gun system includes the gene gun, the tubing prep station, and tubing cutter, in addition to a special helium regulator and hose assembly and an optimization kit with enough materials to prepare nearly 1,000 samples (excluding compressed gases, low-pressure nitrogen regulator, and nucleic acids).

| Transformation Factors | Biolistic Applications | |
| --- | --- | --- |
| | Helio Gene Gun System | PSD-1000/He System |
| Experimental conditions | In situ | In vitro and ex vivo |
| Sample location | External and exposed internal aspects of target organism | Evacuated chamber |
| Target area | Small (2 cm$^2$) | Large (50 cm$^2$) |
| Target membrane structure | In vivo | Fragile to robust |
| Pressure range | 100–600 psi | 450–2,200 psi |
| Type of organism | Animals: rabbit, mouse, monkey, pig, fish, etc., into skin and organs Intact plants: leaves and meristems | Cell culture (adherent animal and plant), embryos, algae, fungi, bacteria |

Alternatively, the following protocol can be utilized for direct in vivo nucleic acid transfer by particle acceleration to achieve systemic expression of the transferred gene. Loose skin and tissues are removed and the area surrounding the wound is prepared to receive a dressing or wound chamber. Creating a flap of epidermis where the deep portion of the flap contains the basal layer of the epidermis can expose target cells located in the hair follicles deep to the epidermal-dermal junction. Alternatively, nucleic acids can be transferred directly into suitable wounds in organs at desired depths by adjusting the delivery voltage or pressure.

The genetic material is then introduced into the target cells, tissue or organ. Briefly, the protein-encoding mRNA is co-precipitated with carrier particles, preferably gold particles, of an appropriate size and shape to enter cells at high velocity after particle acceleration. Preferred particles are gold spheres of between 1 and 3 microns in diameter. During co-precipitation, the mRNA coats the surface of the particles. The coated particles are precipitated in ethanol, washed, resuspended and reversibly deposited on a carrier surface for delivery into a target. The carrier surface can be a flexible sheet, such as a Mylar sheet, or other surface.

Without regard to the type of apparatus used, the deposited particles are then accelerated toward the target. Particle acceleration may be achieved by electric spark discharge, as described in U.S. Pat. No. 5,015,580, which is incorporated herein by reference, or by a gas-driven apparatus. The optimal delivery voltage in an electric spark discharge apparatus depends upon the target animal. Experience has indicated that lower voltages are appropriate for mice and monkeys than for pigs. It has been found that when an electric spark discharge type particle acceleration apparatus is used in pigs a discharge voltage of 25 kV is preferred, although voltages in the range of 15 to 35 kV are adequate to deliver genetic material into skin cells without damaging skin tissue.

Although particle acceleration is the preferred method for delivering mRNA into target cells, mRNA can also be delivered using alternative methods known to those of skill in the art. Lipid-mediated gene transfer has also been described in the art as another means for delivering genetic material into cells. See Felgner, P. L., et al., Lipofection: An Efficient, Lipid Mediated DNA-Transfection Procedure, PNAS USA, 84: 7413–7417 (1987). Lipid-based products can be provided as skin creams containing microscopic liposome spheres with trapped genetic material therein. Other methods for delivering genetic material into cells or tissues include pretreatment of the cells or tissue with a pore-inducing agent such as DMSO followed by direct application of genetic material. Direct topical application, however, is less preferred since it may disrupt wound healing and may deliver the growth factor farther from the true target cells.

Although gene transfer efficiency and expression vary at different organ sites, it is believed that routine optimization of delivery methods into a wound at any location on the organ results in wound healing of the type disclosed herein. It is possible that certain modifications to the nucleic delivery protocol may be desirable to accommodate wounds of particular sizes or depths or variations in condition at particular target sites. Because of the depth control offered by particle acceleration methods, mRNA can be targeted to the keratinocyte layer by adjusting the delivery force, even if no skin flap is created. At 25 kV delivery force, the average particle delivery depth is 60 micrometer in wounds. In intact epidermis, penetration is deeper (100–200 micrometer) when a 25 kV delivery force is used.

The treated cells of the wound are isolated from the external environment both to keep the protein encoded, or induced, by the transferred mRNA localized at the wound site and to keep deleterious agents such as pathogens and dirt out of the wound. The wound site may be covered in a fluid-filled wound treatment chamber that keeps the wound moist and allows the fluid in the chamber to be monitored visually and biochemically during treatment. U.S. Pat. No. 5,152,757, which is incorporated herein by reference, describes one such wound treatment chamber that may be used in conjunction with the present invention. The patent also describes ways in which additives and therapeutics can be added to the wound treatment chamber and ways to monitor wound healing progress visually and biochemically. Other methods for monitoring a wound or keeping a wound clean and moist known to those skilled in the art of treating skin wounds may also be employed if use of a wound chamber is not possible or feasible.

Augmentation of wound healing is assessed using a rodent abdominal wall midline incisional model. Wound healing can be assessed by determining the force required to break the wound during healing; this determination is known as the tensile strength and is expressed in Newtons.

Augmentation of wound healing was investigated using steroid-treated (Table 1), chemotherapy-treated animals (Table 2) or normal animals (Table 3). Steroid treatment with dexamethasone and chemotherapy treatment with doxorubicin resulted in impaired wound healing.

Biolistic treatment of normal and steroid-treated animals was first undertaken with EGF mRNA (Table 1).[12] Surprisingly, a single application of 1 microgram of EGF mRNA to the incision resulted in a significant increase in wound tensile strength at 14 days in the normal animal, and restoration of tensile strength to normal levels in the steroid-treated animals at both 7 and 14 days.

Augmentation of wound healing was observed following biolistic delivery of eIF4E mRNA to the wound site in both the chemotherapy-treated and normal animals. This was the first investigation of eIF4E application of any kind in wound healing.

In the chemotherapy-treated animals (Table 2), biolistic delivery of eIF mRNA raised the tensile strength to the level of normal animals at both 7 and 14 days. Biolistic delivery of EGF mRNA was similarly effective however no additive effect was observed with biolistic delivery of eIF4E mRNA combined with EGF mRNA. This demonstrates for the first time that elevation of eIF4E can have a therapeutic effect.

In the normal animals, biolistic delivery of eIF4E mRNA significantly raised the tensile strength of the wound at both 7 and 14 days (Table 3). This is a true example of accelerated wound healing because the tensile strength of the eIF4E mRNA-treated wound at 7 days was equal to the tensile strength of the wound in normal animals at 14 days. Biolistic delivery of EGF mRNA had no effect on wound healing in the normal animals. However, addition of EGF mRNA to eIF4E mRNA resulted in a significantly increased tensile strength at 14 days as compared to biolistic delivery of eIF4E mRNA alone.

The response of normal animals to mRNA biolistic delivery was assessed by determining the level of EGF found in the wound site during the first 48 hours following biolistic treatment (Table 4). This ELISA assay detects both rat and human EGF. Normal animals that were wounded but did not receive biolistic treatment were used to establish the basal EGF level in the tissue and its response to wounding. In the normal control animals, EGF levels increased during the first 24 hours as expected in response to wounding. Remarkably, biolistic treatment with eIF4E mRNA resulted in a significant increase in tissue EGF that was similar to the elevation of EGF produced by EGF mRNA-biolistic treatment. Therefore, biolistic delivery of eIF4E mRNA increased translation of the endogenous rat EGF mRNA. This confirms the hypothesis that elevating the cellular concentration of eIF4E by biolistic eIF4E mRNA delivery would stimulate translation of endogenous mRNAs to effect augmentation of wound healing. It is also reasonable to assume that eIF4E mRNA-delivery increases the translation of other endogenous mRNAs encoding proteins that mediate wound healing.

The synergistic effect of eIF4E mRNA and EGF mRNA on wound healing at 14 days (Table 3) was accompanied by a synergistic increase in EGF protein (Table 4). It is important to note that the elevation in tissue EGF is considerably more than additive (e.g. at 12 hours the EGF concentration in the combined eIF4E and EGF mRNA treatment was 9.5+0.1, while the added values of eIF4E mRNA and EGF mRNA is only 7.4+0.1). This evidence confirms the hypothesis that eIF4E mRNA delivery increases translation of endogenous mRNAs including EGF.

The time course of EGF elevation (Table 4) suggests that the biolistic treatment with eIF4E mRNA results in a transient short-lived increase in cellular translation that returns to normal within 48 hours. The possibility of this short period of eIF4E elevation resulting in oncogenic transformation appears minimal.

The target cells into which the mRNA is intended to be delivered are cells of human and non-human animals, preferably into mammalian organs such as skin or muscle. This treatment therefore has utility in both human and veterinary therapies where improved wound healing is desired. The invention can also be applied to rapidly healing wounds or to more chronic wounds such as non-healing ulcers, keloids, hypertrophic scars and malignant and non-malignant epidermal diseases. The nature of the wound that one desires to treat can influence the choice of mRNA delivered from among the known genes that encode particular cell growth enhancing proteins.

The mRNA expressing the growth factor, or translation initiation factor, is delivered directly into cells of the tissue or organ. The method of delivering the mRNA into the target cells is not believed to be critical. It is preferred that the mRNA be delivered using accelerated particle technology because the accelerated particle approach facilitates mRNA transfer to a higher proportion of cells than other methods.

The present invention will be more fully understood by reference to the following Examples, which are intended to be merely exemplary of the invention. In the Examples, rats have been used as a model recipient for the mRNA delivery and analysis of wound healing.

EXAMPLES

General Methods

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series*, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference.

For Gene Therapy

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ that is within the recipient. These genetically altered cells have been shown to express the transfected genetic material in situ.

It should be noted that often the natural 5'UTR and/or 3'UTR of the mRNA may be replaced by the 5'UTR and/or 3'UTR of a different gene to enhance translation or stability of the mRNA. Therefore as used herein the mRNA may, as needed, not include the 5'UTR and/or 3'UTR of the actual gene encoding the protein to be expressed by mRNA delivery.

The mRNA can be introduced into cells, tissues or organs by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, particle acceleration, lipofection, and electroporation. Transfection vehicles such as liposomes can also be used to introduce mRNA described above into recipient cells within the inoculated area. Such transfection vehicles are known by one skilled within the art.

Delivery of Gene Products/Therapeutics (Compound)

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered to any tissue or organ site accessible to the mechanism of delivery. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the rat or other experimental animals exemplified herein which treatment has a length proportional to the length of the disease process and therapeutic effectiveness. The doses may be single doses or multiple doses over a period of several days. The treatment generally has a length proportional to the length of the disease process and drug effectiveness and the patient species being treated.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. According to the present invention, however, any vehicle, diluent, or additive used would have to be compatible with the compounds.

Materials and Methods

Animals

Male Harlan Sprague Dawley rats were obtained from Charles River Inc. (Portage, Mich.). All methods and procedures were performed in accordance to the National Institutes of Health Guide for the Care of Laboratory Animals and were approved by the Wayne State University Animal Welfare Committee. Animals were fasted overnight prior to surgery, steroid injection, or chemotherapy injection, and anesthetized with intraperitoneal ketamine (60 mg/kg) and xylazine (8 mg/kg). Steroid-treatment was started 2 days prior to incision and continued daily until sacrifice with Dexamethosone sodium phosphate (16 mg/kg/day). Control animals received saline. For chemotherapy treatment, the hind limbs of rats (average weight 300 g) were shaven and 10 mg/Kg IV Doxorubicin administered through the lateral spahenous vein four days prior to wounding. Normal animals received an equivalent volume of sterile saline and were treated with blank microcarriers.

mRNA

The in vitro transcription plasmid PTCEEC containing the human eIF4E cDNA sequence was provided by Dr. R. E. Rhoads [8]. The hEGF in vitro transcription plasmid encoding a poly(A) tail of 30 residues was constructed [12] with a FLAG epitope inserted between the human Growth Hormone secretory domain and mature human EGF sequence of plasmid pWRG1630 [1]. In vitro transcription was performed using Message Machine In vitro Transcription kits (Ambion Inc., Austin Tex.). In vitro polyadenylation of eIF4e mRNA was carried out with *E. coli* Poly(A) Polymerase (Amersham Pharmacia Biotechnology, Inc. Piscataway, N.J.).

Incisional Wound Model and mRNA Biolistic Delivery

Wound healing was evaluated in a well-characterized standard incisional wound-healing model. Standardized acute incisional wounds were created in the following manner: after induction of anesthesia, the abdomen was shaved, the skin incised with Metzenbaum scissors and retracted, and a midline abdominal incision was made with a scalpel. The incision was immediately closed with a running 3-0-prolene suture. The abdominal incisions were then biolistically treated with microcarriers carrying either 1) no mRNA (blanks), 2) EGF mRNA, 3) eIF4E mRNA or 4) EGF mRNA and eIF4E mRNA. Following treatment, the skin was closed with a running, 4-0 nylon suture, and the animals returned to their housing and allowed chow and water. Animals were euthanized, with an overdose of ketamine and xylazine at either 7 or 14 days for determination of wound bursting strength.

A hand-held BioRad Helios Gene Gun (BioRad Inc., Hercules, Calif.) was used for biolistic delivery of microcarriers. The barrel of the Gene Gun was sterilized and placed directly on the incision. The mRNA was precipitated on to 1.6 micrometer gold microcarriers, and microcarriers precipitated onto tefzel tubing. The Microcarrier Loading Quantity was 0.5 mg microparticles per shot, and the RNA Loading Ratio was 2 micrograms of each mRNA/mg microparticle. This resulted in delivery of 1 microgram of each mRNA per shot. Four adjacent shots were delivered, along the incisional line, at a delivery pressure of 250 psi. Controls consisted of normal, steroid-treated or chemotherapy-treated animals that received the standard incision plus blank microparticle treatment.

Determination of Wound Bursting Strength

The abdominal wall was removed from the euthanized animal for determination of wound bursting strength. After suture removal, two strips of abdominal muscle and fascia, measuring 1 cm wide and 4 cm in length, were excised from the midportion of the wound with a specially constructed tissue harvester. The strips were positioned between the graspers of a DFGS10 force gauge in a TCD200 computer driven tensiometer stand (Chatillon, New York, N.Y.). The tissue was distracted at a constant rate of 20 mm/min and peak wound bursting strength was measured. The wound bursting strength is expressed in Newtons (Tables 1–3).

Quantitation of Tissue EGF Following Biolistic mRNA Delivery

An EGF ELISA kit from Quantikine R&D, Inc. (Minneapolis, Mich.) was used to determine the level of EGF following biolistic delivery of 1.0 microgram of EGF mRNA in the presence or absence of 1.0 microgram of eIF4E mRNA (Table 4). The ELISA detected both endogenous rat EGF and human EGF from the biolistic delivery. Animals were sacrificed at 3, 6, 12, 18, 24 or 48 hours following mRNA delivery. Tissue slices were removed from the incision site and 5 mm diameter tissue punch taken for extraction in lysis buffer. EGF levels were determined by ELISA with the value expressed as pg/ml of tissue lysate.

Example 1

Augmentation of Sound Healing by EGF mRNA Biolistic Delivery in an Animal Model of Normal and Impaired Wound Healing The effect of EGF mRNA biolistic delivery to wound healing in normal and steroid-treated animal was tested (Table 1). Biolistic mRNA treatment of the wound resulted in a significant increase in the wound tensile strength in normal animals 14 days after wounding, however no effect was observed at 7 days. Steroid-treatment impaired wound healing significantly at both 7 and 14 days. Remarkably, EGF mRNA treatment resulted in significant increase in tensile strength in the steroid-treated animals at both 7 and 14 days. EGF mRNA treatment corrected wound healing in the steroid-treated animal to the level observed in normals.

Example 2

Augmentation of Wound Healing by eIF4E mRNA Biolistic Delivery in an Animal Model of Impaired Wound Healing Augmentation of wound healing in animals treated with chemotherapy was used as an example of impaired wound healing (Table 2). Chemotherapy-treated animals received doxorubicin (8 mg/kg) 4 days prior to wounding. The incisions were treated with either 1) blank microcarriers, 2) eIF4E mRNA, 3) EGF mRNA, or 4) eIF4E mRNA+EGF mRNA and analyzed for wound breaking strength determination at 7 and 14 days post-wounding. Animals exposed to chemotherapy demonstrated a significant reduction in wound bursting strength compared to normal animals. Biolistic treatment with eIF4E mRNA or EGF mRNA resulted in augmentation of wound healing to normal levels. No further increase in wound bursting strength was observed in the groups receiving both eIF4E mRNA and EGF mRNA.

Example 3

Augmentation of Wound Healing by eIF4E mRNA Biolistic Delivery in a Normal Animal Model of Wound Healing Augmentation of wound healing in normal healthy animals was tested following biolistic treatment of the incision with either 1) blank microcarriers, 2) EGF mRNA, 3) eIF4E mRNA, or 4) eIF4E mRNA+EGF mRNA (Table 3). Treatment with eIF4E mRNA resulted in a significant increase in the wound tensile strength at both 7 and 14 days. The wound bursting strength of the eIF4E mRNA group at 7 days post-wounding was similar to the wound bursting strength of normal blank microcarrier-treated animals at 14 days post-wounding. This increases in wound tensile strength following eIF4E mRNA delivery is remarkable in that it represents 100% acceleration in wound healing. Such dramatic acceleration of wound healing has great clinical utility.

Treatment with EGF mRNA alone did not augment wound healing at 7 days post-wounding in this study or a previous study (Table 1). Likewise addition of EFG mRNA to eIF4E mRNA had no effect on wound healing at 7 days as the wound bursting strength of the group treated with eIF4E mRNA+EGF mRNA was equivalent to treatment with eIF4e mRNA alone.

In this study, at 14 days post-wounding, no significant effect was observed on wound healing with EGF mRNA alone, however, in another study EGF mRNA delivery demonstrated a significant increase in wound tensile strength at 14 days (Table 1). This is noteworthy in light of the synergistic effect of eIF4E mRNA and EGF mRNA observed at 14 days.

At 14 days post-wounding, animals treated with eIF4E mRNA+hEGF mRNA had a dramatic increase in wound bursting strength. This increase was significantly greater than that observed with eIF4E mRNA. In this group at 14 days, the wound bursting strength of the surgical incisions exceeded the scale of the tensiometer and occasionally would cause rupture in the adjacent tissues; this finding has not previously been demonstrated in the thousands of wounds examined in the laboratory. Indeed, this results in an under estimation of the breaking force at 14 days for the group treated with eIF4E mRNA and EGF mRNA. This observation of eIF4E mRNA and EGF mRNA synergy was surprising and therefore creates great clinical utility if it is replicated in humans.

Example 4

Biolistic Treatment of Wounds in Normal Animals with eIF4E mRNA Elevates Tissue EGF Levels Analysis of normal animals treated with biolistic mRNA delivery was undertaken to detect the level of EGF over a time course following biolistic treatment with 1) no treatment, 2) blank microcarriers, 3) EGF mRNA, 4) eIF4E mRNA or 5) eIF4E mRNA and EGF mRNA (Table 4). The ELISA detected both endogenous rat EGF and human EGF. Animals were sacrificed at 3, 6, 12, 18, 24 or 48 hours following biolistic treatment. The data presented in Table 4 demonstrates that treatment of the wound bed with eIF4E mRNA resulted in a significant increase in tissue EGF concentration, as did treatment with EGF mRNA. Treatment with both eIF4E mRNA and EGF mRNA resulted in a greater increase in EGF tissue levels than either EGF mRNA or eIF4E mRNA.

The time course of EGF elevation suggests that the mRNA biolistic treatment with eIF4E mRNA results in a transient short-lived increase in cellular translation that returns to normal within 48 hours. The possibility of this short period of eIF4E elevation resulting in oncogenic transformation appears minimal.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

TABLE 1

Effect of biolistic application of EGF mRNA to wounds of steroid-treated animals.

| | Tensile Strength (Newtons) | | |
|---|---|---|---|
| Treatment Group (n = 10) | 3 Days | 7 Days | 14 Days |
| Normal Control | 0.8 ± 0.4 | 6.4 ± 2.2 | 10.1 ± 2.2 |
| Normal, Blank | 1.0 ± 0.4 | 6.3 ± 1.7 | 9.6 ± 1.4 |
| Normal, EGF mRNA | 0.7 ± 0.4 | 6.9 ± 0.4 | 14.5 ± 2.0# |
| Steroid, Control | 0.6 ± 0.3 | 4.6 ± 0.9# | 7.5 ± 1.1# |
| Steroid, Blanks | 0.5 ± 0.2 | 5.3 ± 1.0 | 6.5 ± 1.0# |
| Steroid, EGF mRNA | 0.4 ± 0.1 | 6.5 ± 1.4* | 9.3 ± 1.4* | p < 0.05 compared to corresponding normal control group
*p < 0.05 compared to corresponding steroid control group

TABLE 2

Effect of Biolistic Application of EGF mRNA to wounds of chemotherapy-treated animals.

| | Tensile Strength (Newtons) | |
|---|---|---|
| Treatment Group (n = 5) | 7 Days | 14 Days |
| Normal, blank | 4.9 ± 1.2 | 11.7 ± 3.3 |
| Chemotherapy, blank | 2.1 ± 0.8# | 5.7 ± 2.6# |
| Chemotherapy, EGF mRNA | 5.2 ± 1.6* | 11.1 ± 2.9* |
| Chemotherapy, eIF4E mRNA | 7.5 ± 2.1* | 13.9 ± 3.5* |
| Chemotherapy, eIF4E mRNA + EFG mRNA | 7.2 ± 2.2* | 14.2 ± 3.7* | p < 0.05 compared to Normal control group
*p < 0.05 compared to corresponding Chemotherapy-treated group

TABLE 3

Effect of Biolistic Application of eIF4E mRNA to wounds of normal animals.

| | Tensile Strength (Newtons) | |
|---|---|---|
| Treatment Group (n = 4 – 6) | 7 days | 14 days |
| Normal, Blank | 4.5 ± 1.3 | 9.8 ± 3.8 |
| Normal, EGF mRNA | 6.5 ± 2.9 | 11.1 ± 3.3 |
| Normal, eIF4E mRNA | 10.6 ± 2.8* | 13.8 ± 3.9* |
| Normal, eIF4E mRNA + EFG mRNA | 8.4 ± 3.6* | 18.8 ± 3.4#U |

*p < 0.05 compared to Normal control group by ANOVA
p < 0.05 compared to eIF4E-treated group by ANOVA
U underestimation; tissue rupture adjacent to wound

TABLE 4

ELISA data of total EGF levels in normal wounded animals
EGF (pg/ml)

|  | 3 h | 6 h | 12 h | 18 h | 24 h | 48 h |
|---|---|---|---|---|---|---|
| Normal control | 0.5 ± 0.1 | 1.4 ± 0.3 | 1.8 ± 0.1 | 2.2 ± 0.1 | 2.8 ± 0.2 | 2.9 ± 0.3 |
| Normal, Blank | 0.6 ± 0.1 | 1.6 ± 0.3 | 2.3 ± 0.2 | 2.8 ± 0.2 | 3.0 ± 0.1 | 2.7 ± 0.3 |
| EGF mRNA | 1.8 ± 0.1* | 3.6 ± 0.5* | 4.4 ± 0.2* | 5.3 ± 0.8* | 4.6 ± 0.4 | 2.6 ± 0.3 |
| eIF4E mRNA | 1.6 ± 0.2* | 4.3 ± 0.1* | 4.8 ± 0.1* | 6.4 ± 0.3* | 4.6 ± 0.3 | 3.0 ± 0.1 |
| eIF4E mRNA + EGF mRNA | 5.6 ± 0.1# | 7.5 ± 0.1# | 9.5 ± 0.1# | 10.7 ± 0.8# | 5.5 ± 0.4* | 2.5 ± 0.6 |

*$p < 0.05$ compared to normal control
$p < 0.01$ compared to normal control

REFERENCES

1. Andree C, Swain W F, Page C P, Macklin M D, Slama J, Hatzis D, Eriksson E. (1994) Proc Natl Acad Sci USA 91: 12188–12192.
2. Bell G I, Gong N M, Stermien M M. (1986) Nucleic Acid Res 14(21): 8427–8433.
3. Bennett N T, Schultz G S. (1993). Am J Surg 165; 728–734.
4. Brown G L, Curtsinger L J, White M, Mitchell R O, Pietsch J. (1988) Ann Surg 208(6); 788–793.
5. Callis J, Fromm M, Walbot V. (1987) Nucleic Acids Res 15(14): 5823–5831.
6. Cheng L, Ziegelhoffer P R, Yang N-S.(1993) Proc Natl Acad Sci USA 90: 4455–4459.
7. De Benedetti A., Rhodes R. E. (1990) Proc. Natl. Acad. Sci USA 87: 8212–8216
8. Hiremath, L. S.,. Rychlik W, Joshi, S, Domier, L L, Rhoads R E. (1989) J Biol Chem 264: 1132–1138 (published erratum 264:21431).
9. Koromilas, A. E., Lazartis-Karatzas, A., Sonenberg, N. (1992) EMBO J. 11: 4153–4158 (published erratum 11:5138).
10. Lazaris-Karatzas, A. Montine, K. S, Sonenberg, N. (1990) Nature 345: 544–547.
11. Qui P, Ziegelhoffer P, Sun J, Yang N S. (1996). Gene Therapy 3: 262–268.
12. Sohn R. L., Murray M. T., Schwarz, K., Nyitray J., Purray P., Franko A. P., Palmer K., Diebel L. N., Dulcavsky S. A. (2001) Wound Rep. Reg. 9: 287–296.
13. Yang N-S, Burkholder J, Roberts B, Martinell B, McCabe D. (1990) Proc. Natl. Acad. Sci USA 87: 9568–9572.

The invention claimed is:

1. A method of augmenting wound healing by increasing tensile strength of a wound wherein the method comprises directly intracellularly delivering eukaryotic translation initiation factor 4E (eIF4E) mRNA to cells of a wound, thereby potentiating an increase in protein synthesis from endogenous cellular mRNA in said cells and increasing tensile strength of the wound.

2. The method according to claim 1, wherein said potentiating step includes potentiating the increase in protein synthesis of epidermal growth factor from endogenous cellular mRNA in the wound.

* * * * *